US006653103B2

(12) United States Patent
Petersen et al.

(10) Patent No.: US 6,653,103 B2
(45) Date of Patent: Nov. 25, 2003

(54) INHIBITION OF NUCLEOCYTOPLASMIC TRANSPORT BY VESICULAR STOMATITIS VIRUS M PROTEIN-LIKE POLYPEPTIDES

(75) Inventors: Jeannine M. Petersen, Fort Collins, CO (US); Lu-Shiun Her, San Diego, CA (US); James E. Dahlberg, Madison, WI (US); Doreen R. Glodowski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 29 days.

(21) Appl. No.: 10/112,802

(22) Filed: Mar. 29, 2002

(65) Prior Publication Data

US 2003/0086942 A1 May 8, 2003

Related U.S. Application Data

(60) Provisional application No. 60/280,214, filed on Mar. 30, 2001.

(51) Int. Cl.[7] .......................... C12P 21/06; C12Q 1/70; C07K 17/00; C07K 16/00

(52) U.S. Cl. .......................... 435/69.1; 435/5; 530/350; 530/388.21

(58) Field of Search .................... 435/5, 69.1; 530/350, 530/388.21

(56) References Cited

U.S. PATENT DOCUMENTS 5,888,727 A 3/1999 Lund et al.

OTHER PUBLICATIONS

Barge A, Gagnon J, Chaffotte A, Timmins P, Langowski J, Ruigrok RW, Gaudin. Rod–like shape of vesicular stomatitis virus matrix protein. Virology. May 15, 1996;219(2):465–70.

Chen Z, Li Y, Krug RM. Influenza A virus NS1 protein targets poly(A)–binding protein II of the cellular 3'–end processing machinery. EMBO J. Apr. 15, 1999;18(8):2273–83.

Dobbelstein M, Roth J, Kimberly WT, Levine AJ, Shenk T. Nuclear export of the E1B 55–kDa and E4 34–kDa adenoviral oncoproteins mediated by a rev–like signal sequence. EMBO J. Jul. 16, 1997;16(14):4276–84.

Enninga J, Levy DE, Blobel G, Fontoura BM. Role of nucleoporin induction in releasing an mRNA nuclear export block. Science. Feb. 22, 2002;295(5559):1523–5.

Ogden JR, Pal R, Wagner RR. Mapping regions of the matrix protein of vesicular stomatitis virus which bind to ribonucleocapsids, liposomes, and monoclonal antibodies. J Virol. Jun. 1986;58(3):860–8.

Her LS, Lund E, Dahlberg JE. Inhibition of Ran guanosine triphosphatase–dependent nuclear transport by the matrix protein of vesicular stomatitis virus. Science. Jun. 20, 1997;276(5320):1845–8.

Petersen JM, Her LS, Varvel V, Lund E, Dahlberg JE. The matrix protein of vesicular stomatitis virus inhibits nucleocytoplasmic transport when it is in the nucleus and associated with nuclear pore complexes. Mol Cell Biol. Nov. 2000;20(22):8590–601.

Taylor A, Easton AJ, Marriott AC. Matrix protein of Chandipura virus inhibits transcription from an RNA polymerase II promoter. Virus Genes. 1999;19(3):223–8.

Von Kobbe C, van Deursen JM, Rodrigues JP, Sitterlin D, Bachi A, Wu X, Wilm M, Carmo–Fonseca M, Izaurralde E. Vesicular stomatitis virus matrix protein inhibits host cell gene expression by targeting the nucleoporin Nup98. Mol Cell. Nov. 2000;6(5):1243–52.

*Primary Examiner*—Hankyel T. Park
(74) *Attorney, Agent, or Firm*—Quarles & Brady LLP

(57) ABSTRACT

A fragment of vesicular stomatitis virus (VSV) matrix protein (M protein) and M proteins of other viral species that can inhibit nucleocytoplasmic transport of RNA, proteins and RNA-protein complexes are disclosed. These polypeptide products and related polypeptides can be used to inhibit nucleocytoplasmic transport. Further disclosed are fragments of the VSV M protein that can enter into the nucleus of a cell. These fragments and the full length of the VSV M protein can be used to introduce other polypeptides into the nucleus of a cell.

37 Claims, 2 Drawing Sheets

Fig. 1

| | | | |
|---|---|---|---|
| VSV (Orsay) | SEQ ID NO:1 | MSSLKKILG---LKGEGKKSKK------LGIAESPMEEDTNMEYAPSAEIDKSYFGVDEMDTHD | 55 |
| CV | SEQ ID NO:2 | MQRLKKFIA---KPEKGDKGRMKWNS-SMDYDSESQDVRR-GIFPTDLFG---MEDDMEFTP | 58 |
| PV | SEQ ID NO:3 | MKSIRQLLSLAKEEKKREKKSNHGSHSMEWESPSNEIKS----PSAEIFG---YDYEDMEYLP | 58 |
| SVCV | SEQ ID NO:4 | MSTLRKLFG-TKKSKG----------------TETKEETLA-----TRML------MDTHD | 35 |
| PhD | | HHHHHHH EE | |
| Predator | | HHHHHHH | |

| | | | |
|---|---|---|---|
| VSV (Orsay) | SEQ ID NO:1 | PHQLRYEKFETVKMTVRSNREERTYSEVAAAVSHDHMEIEMAGERPEEKIDAFLGSSNDKA | 118 |
| CV | SEQ ID NO:2 | SLGIQTLKDQYKCVMNAIMEERDFREAISAMQFESLDADSYIGENKPERAILHTARQLET | 121 |
| PV | SEQ ID NO:3 | TLGVQTLKLQYKCVEDQVRSESEETSYLDAVDNVANNEKQSNGFSGAKPEVRAVMVRAVQAMEA | 121 |
| SVCV | SEQ ID NO:4 | THSHSLQWMREYHVEDDKLDTESLLGLERNMDVDKESRNMREVRLEMFRCALEDEH | 98 |
| PhD | | HHHHHHHEEE EEEEEE HHHHHHHHH:HHHH | |
| Predator | | HHHHHHHH HHEEEE HHHH HHHHHHHH;HHHH | |

| | | | |
|---|---|---|---|
| VSV (Orsay) | SEQ ID NO:1 | TPAVLADQGPEEHAHCEGRAYEPHRMEKTEPMLNVPEYERRPFNVGLYKETVELTETETYDDE | 181 |
| CV | SEQ ID NO:2 | SNPGILDRGVVEEHATTOGRALMFHSLQPSEEMFVPETTREWNILTNKESTINVKIMLGETD | 184 |
| PV | SEQ ID NO:3 | NPMSLQDGRSPEMTSEIEERCLMFHSLEHIPMYMCEQFTRDWSGRRNQEIVNVKIMVGVTD | 184 |
| SVCV | SEQ ID NO:4 | VSGTYSVDGSALESNKVQESCYMPEREEQMEPEKREIEVERYPVHQHGYNEMAVDLRMSICDLN | 161 |
| PhD | | EEEE E EE EEEEEEE H | |
| Predator | | EEEEEE EEEEEE | |

| | | | |
|---|---|---|---|
| VSV (Orsay) | SEQ ID NO:1 | SLEAAPMEIWDHFNSSKFSDEREKALMFEIVEKKASGAWVLDSVSHFK------- | 229 |
| CV | SEQ ID NO:2 | TLSELEFELLNPVNFRDDREMIEGAAIMEEIKKQKDNTWLIISKSH-------- | 229 |
| PV | SEQ ID NO:3 | TLDNLDQEIFDPKEHFSEEEMLSAATILEEVKKSSDNNYIISKSY--------- | 229 |
| SVCV | SEQ ID NO:4 | GEKIGLNELKECEVAHPNHEQKYLEEVEEAACSATGEWIDWTFPMPVDVVPRVPSLFMGD | 223 |
| PhD | | HHHHHHHHHH EEEEE EEEEE | |
| Predator | | H HHHHHHHHHEEE EE | |

```
        13              2425 27              39 40            51
MSSLKKILGLKGKGKKSKKLGIAPPPYEEDTNMEYAPSAPIDKSYFGVDEMDTHDPH    SEQ ID NO: 5
|                     |         |                  |        |
1                     22        32                 47       57
```

M 1-22
M 1-47
M 1-57
M 23-57
M 32-57
M 23-47

SEQUENCE LISTING

<160> NUMBER OF SEQ ID NOS: 75

<210> SEQ ID NO 1
<211> LENGTH: 229
<212> TYPE: PRT
<213> ORGANISM: Vesicular stomatitis virus (Orsay strain)

<400> SEQUENCE: 1

Met Ser Ser Leu Lys Lys Ile Leu Gly Leu Lys Gly Lys Gly Lys Lys
1               5                   10                  15

Ser Lys Lys Leu Gly Ile Ala Pro Pro Tyr Glu Glu Asp Thr Asn

```
                    20                  25                  30
Met Glu Tyr Ala Pro Ser Ala Pro Ile Asp Lys Ser Tyr Phe Gly Val
             35                  40                  45

Asp Glu Met Asp Thr His Asp Pro His Gln Leu Arg Tyr Glu Lys Phe
 50                  55                  60

Phe Phe Thr Val Lys Met Thr Val Arg Ser Asn Arg Pro Phe Arg Thr
 65                  70                  75                  80

Tyr Ser Glu Val Ala Ala Val Ser His Trp Asp His Met Tyr Ile
             85                  90                  95

Gly Met Ala Gly Lys Arg Pro Phe Tyr Lys Ile Leu Ala Phe Leu Gly
             100                 105                 110

Ser Ser Asn Leu Lys Ala Thr Pro Ala Val Leu Ala Asp Gln Gly Gln
             115                 120                 125

Pro Glu Tyr His Ala His Cys Glu Gly Arg Ala Tyr Leu Pro His Arg
 130                 135                 140

Met Gly Lys Thr Pro Pro Met Leu Asn Val Pro Glu Tyr Phe Arg Arg
145                 150                 155                 160

Pro Phe Asn Val Gly Leu Tyr Lys Gly Thr Val Glu Leu Thr Met Thr
                 165                 170                 175

Ile Tyr Asp Asp Glu Ser Leu Glu Ala Ala Pro Met Ile Trp Asp His
             180                 185                 190

Phe Asn Ser Ser Lys Phe Ser Asp Phe Arg Glu Lys Ala Leu Met Phe
             195                 200                 205

Gly Leu Ile Val Glu Lys Lys Ala Ser Gly Ala Trp Val Leu Asp Ser
             210                 215                 220

Val Ser His Phe Lys
225

<210> SEQ ID NO 2
<211> LENGTH: 229
<212> TYPE: PRT
<213> ORGANISM: Chandipura virus

<400> SEQUENCE: 2

Met Gln Arg Leu Lys Lys Phe Ile Ala Lys Arg Glu Lys Gly Asp Lys
 1               5                  10                  15

Gly Lys Met Lys Trp Asn Ser Ser Met Asp Tyr Asp Ser Pro Pro Ser
             20                  25                  30

Tyr Gln Asp Val Arg Arg Gly Ile Phe Pro Thr Ala Pro Leu Phe Gly
             35                  40                  45

Met Glu Asp Asp Met Met Glu Phe Thr Pro Ser Leu Gly Ile Gln Thr
 50                  55                  60

Leu Lys Leu Gln Tyr Lys Cys Val Val Asn Ile Asn Ala Ile Asn Pro
 65                  70                  75                  80

Phe Arg Asp Phe Arg Glu Ala Ile Ser Ala Met Gln Phe Trp Glu Ala
             85                  90                  95

Asp Tyr Ser Gly Tyr Ile Gly Lys Lys Pro Phe Tyr Arg Ala Ile Ile
             100                 105                 110

Leu His Thr Ala Arg Gln Leu Lys Thr Ser Asn Pro Gly Ile Leu Asp
             115                 120                 125

Arg Gly Val Val Glu Tyr His Ala Thr Thr Gln Gly Arg Ala Leu Val
 130                 135                 140

Phe His Ser Leu Gly Pro Ser Pro Ser Met Met Phe Val Pro Glu Thr
145                 150                 155                 160
```

-continued

```
Phe Thr Arg Glu Trp Asn Ile Leu Thr Asn Lys Gly Thr Ile Asn Val
                165                 170                 175

Lys Ile Trp Leu Gly Glu Thr Asp Thr Leu Ser Glu Leu Glu Pro Ile
            180                 185                 190

Leu Asn Pro Val Asn Phe Arg Asp Asp Arg Glu Met Ile Glu Gly Ala
        195                 200                 205

Ala Ile Met Gly Leu Glu Ile Lys Lys Gln Lys Asp Asn Thr Trp Leu
    210                 215                 220

Ile Ser Lys Ser His
225

<210> SEQ ID NO 3
<211> LENGTH: 229
<212> TYPE: PRT
<213> ORGANISM: Piry virus

<400> SEQUENCE: 3

Met Lys Ser Ile Arg Gln Leu Leu Ser Leu Ala Lys Lys Glu Lys Lys
  1               5                  10                  15

Arg Glu Lys Lys Ser Asn His Gly Ser His Ser Met Glu Trp Glu Ser
            20                  25                  30

Pro Pro Ser Tyr Asn Glu Ile Lys Ser Pro Ser Ala Pro Ile Phe Gly
        35                  40                  45

Tyr Asp Tyr Glu Asp Met Glu Tyr Leu Pro Thr Leu Gly Val Gln Thr
    50                  55                  60

Leu Lys Leu Gln Tyr Lys Cys Val Leu Gln Val Arg Ser Glu Ser Pro
65                  70                  75                  80

Phe Thr Ser Tyr Leu Asp Ala Val Asp Asn Val Ala Asn Trp Glu Lys
                85                  90                  95

Gln Tyr Asn Gly Phe Ser Gly Lys Lys Pro Phe Tyr Arg Ala Val Met
            100                 105                 110

Val Arg Ala Val Gln Ala Met Lys Ala Asn Pro Met Ser Leu Gln Asp
        115                 120                 125

Gly Arg Ser Pro Glu Tyr Thr Ser Glu Ile Glu Gly Arg Cys Leu Val
    130                 135                 140

Phe His Ser Leu Gly His Ile Pro Pro Met Met Tyr Met Cys Glu Gln
145                 150                 155                 160

Phe Thr Arg Asp Trp Ser Gly Arg Arg Asn Gln Gly Ile Val Asn Val
                165                 170                 175

Lys Ile Trp Val Gly Val Thr Asp Thr Leu Asp Asn Leu Asp Gln Ile
            180                 185                 190

Phe Asp Pro Lys Lys His Phe Ser Glu Glu Glu Met Leu Ser Ala Ala
        195                 200                 205

Thr Ile Leu Gly Leu Glu Val Lys Lys Ser Ser Asp Asn Asn Tyr Ile
    210                 215                 220

Ile Ser Lys Ser Tyr
225

<210> SEQ ID NO 4
<211> LENGTH: 223
<212> TYPE: PRT
<213> ORGANISM: Spring viremia carp virus

<400> SEQUENCE: 4

Met Ser Thr Leu Arg Lys Leu Phe Gly Thr Lys Lys Ser Lys Gly Thr
  1               5                  10                  15
```

```
Pro Pro Thr Tyr Glu Glu Thr Leu Ala Thr Ala Pro Val Leu Met Asp
            20                  25                  30

Thr His Asp Thr His Ser His Ser Leu Gln Trp Met Arg Tyr His Val
        35                  40                  45

Glu Leu Asp Val Lys Leu Asp Thr Pro Leu Lys Thr Met Ser Asp Leu
    50                  55                  60

Leu Gly Leu Leu Lys Asn Trp Asp Val Asp Tyr Lys Gly Ser Arg Asn
65                  70                  75                  80

Lys Arg Arg Phe Tyr Arg Leu Ile Met Phe Arg Cys Ala Leu Glu Leu
                85                  90                  95

Lys His Val Ser Gly Thr Tyr Ser Val Asp Gly Ser Ala Leu Tyr Ser
            100                 105                 110

Asn Lys Val Gln Gly Ser Cys Tyr Val Pro His Arg Phe Gly Gln Met
        115                 120                 125

Pro Pro Phe Lys Arg Glu Ile Glu Val Phe Arg Tyr Pro Val His Gln
    130                 135                 140

His Gly Tyr Asn Gly Met Val Asp Leu Arg Met Ser Ile Cys Asp Leu
145                 150                 155                 160

Asn Gly Glu Lys Ile Gly Leu Asn Leu Leu Lys Glu Cys Gln Val Ala
                165                 170                 175

His Pro Asn His Phe Gln Lys Tyr Leu Glu Glu Val Gly Leu Glu Ala
            180                 185                 190

Ala Cys Ser Ala Thr Gly Glu Trp Ile Leu Asp Trp Thr Phe Pro Met
        195                 200                 205

Pro Val Asp Val Val Pro Arg Val Pro Ser Leu Phe Met Gly Asp
    210                 215                 220

<210> SEQ ID NO 5
<211> LENGTH: 57
<212> TYPE: PRT
<213> ORGANISM: Vesicular stomatitis virus (Orsay strain)

<400> SEQUENCE: 5

Met Ser Ser Leu Lys Lys Ile Leu Gly Leu Lys Gly Lys Gly Lys Lys
1               5                   10                  15

Ser Lys Lys Leu Gly Ile Ala Pro Pro Tyr Glu Glu Asp Thr Asn
            20                  25                  30

Met Glu Tyr Ala Pro Ser Ala Pro Ile Asp Lys Ser Tyr Phe Gly Val
        35                  40                  45

Asp Glu Met Asp Thr His Asp Pro His
    50                  55

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gggctgcaga gatctccgc                                              19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
``` oligonucleotide

<400> SEQUENCE: 7
ggagatctct gcagccccgc                                                        20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 8
gtctatggcc atcatacgtt a                                                      21

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence:PCR primer

<400> SEQUENCE: 9
cgggatccaa gagcgtaatc tggaacatcg tatgggtaac gcggaaccag atccg            55

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 10
catcatggga tccttaaaga aagattctcg g                                           31

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 11
cgggatccat gcggatcatg agtgtcc                                                27

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 12
catcatggga tccttaaaga aagattctcg g                                           31

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:PCR primer

<400> SEQUENCE: 13
aaggatccga tccctaattt c                                                      21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 14
cgggatccgc accacccct tatg                                    24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 15
cgggatccat gcggatcatg agtgtcc                                27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 16
tgggatccat ggagtatgct ccgagcg                                27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 17
cgggatccat gcggatcatg agtgtcc                                27

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 18
cgggatccgc accacccct tatg                                    24

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 19
cgggatcctc caaaatagga tttgtcaatt                             30

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:PCR primer

```
<400> SEQUENCE: 20
cgggatccgg agttgacgag atggac                                          26

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 21
gggagctcgc ccgggatcc                                                  20

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 22
cgggatccca tcaattaaga tatgagaaaa a                                    31

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 23
gggagctcgc ccgggggat cc                                               22

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:PCR primer

<400> SEQUENCE: 24
cgggatccgg agttgacgag atggac                                          26

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 25
cgggatccat tgaaatcatc ccagatc                                         27

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
ctaagaaatt agggatcgca gcacccccctt atgaagagga c                        41

<210> SEQ ID NO 27
```

<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
gtcctcttca taaggggtg ctgcgatccc taatttctta g        41

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
gaaattaggg atcgcaccag ccccttatga agaggacac          39

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gtgtcctctt cataaggggc tggtgcgatc cctaatttc          39

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
gggatcgcac caccccctgc tgaagaggac actaac            36

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gttagtgtcc tcttcagcag ggggtggtgc gatccc            36

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
ggagtatgct ccgagccttc caatgacaaa tcctattttg g      41

<210> SEQ ID NO 33
<211> LENGTH: 42

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
ccaaaatagg atttgtcaat tggaaggctc ggagcatact cc                    42

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
ggagtatgct ccgagcgctg caattgacaa atcctatttt gg                    42

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
ccaaaatagg atttgtcaat tgcagcgctc ggagcatact cc                    42

<210> SEQ ID NO 36
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
cctattttgg agttgacgag gcggacactc atgatccgc                        39

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
cctattttgg agttgacgag gcggacactc atgatccgc                        39

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38
gacggttaga tctaatcgtg cgttcagaac atactcagaa g                     41

<210> SEQ ID NO 39
<211> LENGTH: 41
<212> TYPE: DNA
```

<213> ORGANISM: Artificial Sequence
<220> FEATURE:
<223> OTHER INFORMATION: Description of Artificial Sequence:
      oligonucleotide

<400> SEQUENCE: 39
cttctgagta tgttctgaac gcacgattag atctaaccgt c                    41

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
ggcagccgct gtatcccatg cggatcacat gtacatcgg                       39

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
ccgatgtaca tgtgatccgc atgggataca gcggctgcc                       39

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gtatcccatt gggatcacat ggccatcgga atggcaggga aacg                 44

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
cgtttccctg ccattccgat ggccatgtga tcccaatggg atac                 44

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
gggatcacat gtacatcgca atggcaggga aacgtccc                        38

<210> SEQ ID NO 45
<211> LENGTH: 38
<212> TYPE: DNA
<213> ORGANISM: Artificial Sequence

```
<220> FEATURE:
<223> OTHER INFORMATION: Description of Artificial Sequence:
      oligonucleotide

<400> SEQUENCE: 45
gggacgtttc cctgccattg cgatgtacat gtgatccc                                38

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 46
catcggaatg gcaggggcac gtcccttcta caagatc                                 37

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 47
gatcttgtag aagggacgtg cccctgccat tccgatg                                 37

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 48
ggcagggaaa cgtcccgcct acaagatctt ggcttttttg gg                           42

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 49
cccaaaaaag ccaagatctt gtaggcggga cgtttccctg cc                           42

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 50
gcagggaaac gtcccttcgc caagatcttg gctttttgg g                             41

<210> SEQ ID NO 51
<211> LENGTH: 41
<212> TYPE: DNA
<213> ORGANISM: Artificial Sequence
<220> FEATURE:
```

<223> OTHER INFORMATION: Description of Artificial Sequence:
      oligonucleotide

<400> SEQUENCE: 51
cccaaaaaag ccaagatctt ggcgaaggga cgtttccctg c                              41

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 52
gcagggaaac gtcccttctt caagatcttg cttttttgg g                              41

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 53
cccaaaaaag ccaagatctt gaagaaggga cgtttccctg c                              41

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 54
gggttcttct aatctagcgg ccactccagc ggtattggc                                 39

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 55
gccaataccg ctggagtggc cgctagatta gaagaaccc                                 39

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 56
gatcaaggtc aaccagaggc tcacgctcac tgtgaaggc                                 39

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence:

oligonucleotide

<400> SEQUENCE: 57
gccttcacag tgagcgtgag cctctggttg accttgatc         39

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 58
gtatcacgct cactgtgaag ccagggctta tttgccacac        40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 59
gtgtggcaaa taagccctgg cttcacagtg agcgtgatac        40

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 60
ggcagggctt atttgccagc cagaatgggg aagacccctc cc     42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 61
gggaggggtc ttccccattc tggctggcaa ataagccctg cc     42

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 62
gcttatttgc cacacagaat ggcgaagacc cctcccatgc        40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 63
gcatgggagg ggtcttcgcc attctgtgtg gcaaataagc                    40

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 64
cacagaatgg ggaagaccgc tcccatgctc aatgtacc                     38

<210> SEQ ID NO 65
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 65
ggtacattga gcatgggagc ggtcttcccc attctgtg                     38

<210> SEQ ID NO 66
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 66
cccatgctca atgtaccagc gcacttcaga agaccattc                    39

<210> SEQ ID NO 67
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 67
gaatggtctt ctgaagtgcg ctggtacatt gagcatggg                    39

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 68
gctcaatgta ccagagcacg ccagaagacc attcaatg                     38

<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 69
cattgaatgg tcttctggcg tgctctggta cattgagc                        38

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 70
caatgtaggt ctttacaagg caacggttga gctcac                          36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 71
gtgagctcaa ccgttgcctt gtaaagacct acattg                          36

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 72
gagaaggcct taatgtttgc cctgattgtc gagaaaaagg c                    41

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 73 gccttttttct cgacaatcag ggcaaacatt aaggccttct c                   41

<210> SEQ ID NO 74
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 74
gaaggcctta atgtttggcg cgattgtcga gaaaaaggc                       39

<210> SEQ ID NO 75
<211> LENGTH: 39
<212> TYPE: DNA
```

-continued

```
<213> ORGANISM: Artificial Sequence
<220> FEATURE:
<223> OTHER INFORMATION: Description of Artificial Sequence:
      oligonucleotide

<400> SEQUENCE: 75
gcctttttct cgacaatcgc gccaaacatt aaggccttc                              39
```

INHIBITION OF NUCLEOCYTOPLASMIC TRANSPORT BY VESICULAR STOMATITIS VIRUS M PROTEIN-LIKE POLYPEPTIDES

CROSS-REFERENCE TO RELATED APPLICATIONS

This application claims priority to U.S. Ser. No. 60/280,214, filed on Mar. 30, 2001 which is incorporated by reference herein as if fully set forth.

STATEMENT REGARDING FEDERALLY SPONSORED RESEARCH OR DEVELOPMENT

This invention was made with United States government support awarded by the following agency: NIH Grant No. GM30220. The United States has certain rights in this invention.

BACKGROUND OF THE INVENTION

Trafficking of macromolecules between the nucleus and the cytoplasm occurs through nuclear pore complexes (NPCs), large proteinaceous structures (>50 different proteins) that perforate the nuclear envelope. Many small molecules (<40 kDa) can diffuse through NPCs, but large molecules must be transported across NPCs via carrier-mediated and signal-dependent processes. Much of the import and export of molecules across NPCs involves the interaction of transport receptors with their cargoes, the RanGTPase, and components of the NPC (1, 2).

Transport receptors, termed importins and exportins (or karyopherins), bind their appropriate cargoes directly or via specialized adaptor proteins (3). Once these complexes have formed, movement through the NPCs proceeds by a process involving sequential interactions of the receptor-cargo complexes with docking sites on the nuclear pore proteins (nucleoporins). A number of nucleoporins, particularly those containing phenylalanine-glycine (FG) repeat motifs, have been shown to interact directly with transport receptors (4). RanGTPase, which binds to transport receptors, plays a critical role in transport by promoting the association of cargo with export receptors as well as the dissociation of cargo from import receptors. Hydrolysis of RanGTP in the cytoplasm and regeneration of RanGTP in the nucleus sustains a gradient of RanGTP across the nuclear envelope, resulting in delivery of the transport cargoes to the appropriate cell compartments (5, 6).

Carrier-mediated movement across NPCs can be blocked in a variety of ways. Inactivation of RanGTPase leads to a block of most nucleocytoplasmic transport (7). Also, interference with the interactions between receptor-cargo complexes and nucleoporins inhibits nuclear transport. The lectin wheat germ agglutinin, which binds to O-glycosylated nucleoporins, blocks both import and export across NPCs (8), and antibodies to Nup98 or Nup153, two FG repeat-containing components of the NPC, block the export of small nuclear RNAs (snRNAs) and mRNA (9, 10). Likewise, the isolated nucleoporin binding domains of the transport factors importin β and TAP inhibit the export of mRNA and snRNAs (11, 12). This domain of importin β is also an efficient inhibitor of protein import.

Infection of eukaryotic cells by viruses can affect the nucleocytoplasmic transport of host-cell proteins and RNAs (13–15). Previously, we and others have demonstrated that the matrix (M) protein of vesicular stomatitis virus (VSV) is a potent inhibitor of nuclear transport (15, 16, and U.S. Pat. No. 5,888,727). M protein, a structural component of VSV virions, blocks the nuclear export of snRNAs and spliced mRNAs as well as the nuclear import of small nuclear ribonucleoproteins (snRNPs) (15 and U.S. Pat. No. 5,888,727). However, it was not known whether a fragment of the VSV M protein could retain its nucleocytoplasmic transport inhibition activity. It was not known either whether M proteins of other viral species had similar nucleocytoplasmic transport inhibition activities.

BRIEF SUMMARY OF THE INVENTION

In one embodiment, the invention is summarized in that a fragment of the VSV M protein and M proteins of other viral species have been demonstrated to have nucleocytoplasmic transport inhibition activity. A methionine conserved in the VSV M protein and M proteins of other viral species mentioned above has been shown to be important for transport inhibition activity of these proteins. Fragments of VSV M proteins that can enter into the nucleus of a cell have also been identified.

In one aspect, the present invention is an isolated M protein-like polypeptide having an amino acid sequence that is at least 26% similar to amino acids 47–229 of SEQ ID NO:1 (VSV M protein amino acid sequence), wherein the amino acid sequence contains methionine at a position corresponding to position 51 of SEQ ID NO:1.

In another aspect, the present invention is an isolated M protein gene-like polynucleotide having a nucleotide sequence that encodes a polypeptide at least 26% similar to amino acids 47–229 of SEQ ID NO:1, wherein the amino acid sequence contains methionine at a position corresponding to position 51 of SEQ ID NO:1. The polypeptide-encoding nucleotide sequence can be operably linked to a promoter to control the expression of the polypeptide.

In another aspect, the present invention is a vector or a host cell that contains the M protein gene-like polynucleotide described above.

In another aspect, the present invention is a method for inhibiting transport of RNA, proteins or RNA-protein complexes between nucleus and cytoplasm of a cell. The method involves exposing the cell to sufficient quantity of a VSV M protein-like polypeptide having an amino acid sequence that is at least 26% similar to amino acids 47–229 of SEQ ID NO:1, wherein the amino acid sequence contains methionine at a position corresponding to position 51 of SEQ ID NO:1.

In another aspect, the present invention is a method of inhibiting import of proteins or RNA-protein complexes from cytoplasm into nucleus of a cell. The method involves exposing the cell to sufficient quantity of a VSV M protein-like polypeptide having an amino acid sequence that is at least 26% similar to amino acids 47–229 of SEQ ID NO:1, wherein the amino acid sequence contains methionine at a position corresponding to position 51 of SEQ ID NO:1.

In another aspect, the present invention is a method of inhibiting export of nucleic acids from nucleus to cytoplasm of a cell. The method involves exposing the cell to sufficient quantity of a VSV M protein-like polypeptide having an amino acid sequence that is at least 26% similar to amino acids 47–229 of SEQ ID NO:1, wherein the amino acid sequence contains methionine at a position corresponding to position 51 of SEQ ID NO:1.

In a related aspect, the present invention is a method for inhibiting transport of RNA, proteins or RNA-protein complexes between nucleus and cytoplasm of a cell. The method involves first analyzing an amino acid sequence that is at least 26% similar to amino acids 47–229 of SEQ ID NO:1 to identify a smaller fragment that retains the ability to inhibit nucleocytoplasmic transport, wherein sized fragments of the amino acid sequence are compared to determine which segments of the amino acid sequence can be deleted without loss of transport inhibition function. The next step of the method involves exposing a cell to sufficient quantity of a VSV M protein-like polypeptide which contains the smaller fragment such that transport of RNA, proteins or RNA-protein complexes across the nuclear envelope is inhibited.

In another related aspect, the present invention is a method for screening for an agent that can alter the activity of an M protein. The first step of the method involves introducing into the nucleus of a cell a VSV M protein-like polypeptide having an amino acid sequence that is at least 26% similar to amino acids 47–229 of SEQ ID NO:1, wherein the amino acid sequence contains methionine at a position corresponding to position 51 of SEQ ID NO:1 and wherein the polypeptide inhibits the nucleocytoplasmic transport of the cell. The method next involves exposing the cell to a test agent and determining the nucleocytoplasmic transport rate of a molecule before and after exposing the cell to the agent, wherein the molecule is selected from a RNA, a protein and a RNA-protein complex.

In another aspect, the present invention is a method for identifying a nuclear import element. The first step of the method involves exposing a cell to sufficient quantity of an M protein-like polypeptide which comprises an amino acid sequence that is at least 26% similar to amino acids 47–229 of SEQ ID NO:1, wherein the amino acid sequence contains methionine at a position corresponding to position 51 of SEQ ID NO:1, so that import of proteins from cytoplasm into the nucleus is inhibited. The method next involves selecting a protein molecule that is imported in the presence of the M protein-like polypeptide and examining the imported molecule for the presence of a polypeptide that can function as a nuclear export element when attached to another protein.

In another aspect, the present invention is a method for identifying a nuclear export element. The first step of the method involves exposing a cell to sufficient quantity of an M protein-like polypeptide having an amino acid sequence that is at least 26% similar to amino acids 47–229 of SEQ ID NO:1, wherein the amino acid sequence contains methionine at a position corresponding to position 51 of SEQ ID NO:1, so that export of RNA between the nucleus and cytoplasm is inhibited. The method next involves selecting an RNA molecule that is exported in the presence of the M protein-like polypeptide and examining the molecule for the presence of a nuclear export element.

In another aspect, the present invention is a polypeptide of amino acids 1–57 of VSV M protein or amino acids 23–57 of VSV M protein. A polynucleotide encoding the polypeptide is also within the scope of the present invention.

In another aspect, the present invention is a chimeric protein containing a non-M protein polypeptide and a polypeptide having an amino acid sequence selected from amino acids 1–229 of VSV M protein, amino acids 47–229 of VSV M protein, amino acids 1–57 of VSV M protein, and amino acids 23–57 of VSV M protein. A polynucleotide having a nucleotide sequence that encodes the chimeric protein is also within the scope of the present invention.

In another aspect, the present invention is a method for introducing a non-M protein polypeptide into the nucleus of a cell. The method involves linking the non-M protein polypeptide to a polypeptide having an amino acid sequence selected from amino acids 1–229 of VSV M protein, amino acids 47–229 of VSV M protein, amino acids 1–57 of VSV M protein, and amino acids 23–57 of VSV M protein.

BRIEF DESCRIPTION OF THE SEVERAL VIEWS OF THE DRAWINGS

FIG. 1 is a sequence alignment and predicted secondary structure of M proteins from VSV (Orsay strain), Chandipura Virus (CV), Piry Virus (PV), and Spring Viremia Carp Virus (SVCV) using the CLUSTAL W program. Identical amino acids are indicated in gray boxes, and conserved amino acids are shown in clear boxes. The M proteins from CV:PV, CV:VSV, CV:SVCV, PV:VSV, PV:SVCV, and VSV:SVCV are 70.3%, 51.5%, 42.3%, 48.9%, 46.3%, and 49.8% similar, respectively. Secondary structure predictions from the PREDATOR and PH.D. programs are indicated below the alignment as alpha helices (H) and beta strands (E). * indicates a conserved methionine that is essential for the inhibitory function of the M proteins.

DETAILED DESCRIPTION OF THE INVENTION

Figures 2A, 2B:
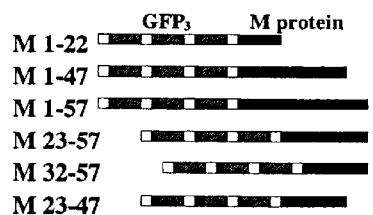
FIG. 2 shows the amino acid sequence of VSV M protein amino acids 1–57 (A) and protein truncation constructs used in the present invention for determining nuclear localization signals (NLS) (B). In (A), amino acids identified by sequence alignment (FIG. 1) as being identical among M proteins of VSV, CV, SVCV and PV are in boldface, with the number of each amino acid position indicated above. Amino acids 23–57 are underlined. The region common to both M 23–57 and M 47–229 is underlined twice. In (B), dark boxes represent VSV M protein regions of fusion proteins, while lined boxes represent GFP3 region of fusion proteins. GFP3 region is not drawn to scale.

The present invention discloses that a fragment of VSV M protein from amino acid 47 to amino acid 229 (VSV M protein amino acid sequence is provided as SEQ ID NO:1) retains the nucleocytoplasmic transport inhibition activity of the full length VSV M protein. Amino acid 91 and amino acid 105 of the VSV M protein are important for nuclear localization of the fragment. Once in the nucleus of a cell, amino acids at these two positions become less critical for the transport inhibition activity of the fragment.

The present invention also discloses that M proteins from other vesiculoviruses such as CV and SVCV can enter into the nucleus of a cell and inhibit nucleocytoplasmic transport. Methionine at amino acid position 51 of VSV M protein and corresponding positions of CV and SVCV M proteins is necessary for nucleocytoplasmic transport inhibition activity of these proteins. It is anticipated that M proteins from other vesiculoviruses such as PV that have a methionine corresponding to methionine 51 of the VSV M protein possess similar transport inhibition activities. As a group, the full length vesiculovirus M proteins share 11% identity and 29% similarity of amino acids. For the region corresponding to amino acids 47–229 of the VSV M protein, vesiculovirus M proteins share 26% similarity. M proteins do not show homology to other proteins. Thus, it is anticipated that a polypeptide that is as little as 26% similar to the VSV M protein and has the important methionine described above may be used to inhibit nucleocytoplasmic transport.

Further disclosed in this invention are fragments of VSV M protein that can enter into the nucleus of a cell. These fragments include, in addition to the fragment of amino acids 47–229 already described above, amino acids 1–57 and amino acids 23–57.

For the purpose of the present invention, one determines the percentage of identity and similarity between amino acids 47–229 of SEQ ID NO:1 and another amino acid sequence by first aligning the two sequences using the CLUSTAL W program (can be found at the following website:http://www.ebi.ac.uk/clustalw/) as of the filing date of the present application. The alignment can be generated either with the program's default settings or with settings to maximize the number of identical amino acids between the two sequences. An article describing the CLUSTAL W method can be found at http://bimas.dcrt.nih.gov/clustalw/clustalw.html. Amino acid identity occurs when the same amino acid is present at corresponding positions of the two sequences. Similarity occurs when similar amino acids are present at corresponding positions of the two sequences. Next, identity and similarity percentages are calculated by dividing the number 183 (the total number of amino acids from amino acids 47–229 of SEQ ID NO:1) into the number of positions from one of the two sequences that show identity or similarity and multiplying by 100. For the purpose of the present invention, similar amino acids are those with similar side chains in terms of chemical properties. For example, amino acids that have aliphatic, aromatic, basic or acidic side chains are considered similar amino acids; similar amino acid groups, by way of example, would include alanine, valine, leucine, and isoleucine; phenylalanine, tyrosine, and tryptophan; lysine, arginine, and histidine; aspartate and glutamate, respectively.

In the specification and claims, the term "inhibiting" used in the context of inhibiting nucleocytoplasmic transport means reducing transport rate. Thus, an inhibition can be 100% or less than 100%.

The term "VSV M protein-like polypeptide" used in the specification and claims can be a fragment of the VSV M protein containing amino acids 47–229, a homologous M protein from another viral species, a non-natural protein possessing the nucleocytoplasmic transport inhibition activity of the VSV M protein, and any of the foregoing with additional amino acids attached in a fashion not seen in naturally occurring M proteins. "VSV M protein-like polypeptide" used herein does not include the VSV M protein itself.

In the specification and claims, the term "M protein-like polypeptide" is used to mean a polypeptide that is related to a full length native M protein but is not one of the full length native M proteins.

The term "non-M protein polypeptide" is used in the specification and claims to mean a polypeptide that is not one of the full length native M proteins or a fragment thereof.

The term "M protein gene-like polynucleotide" is used in the specification and claims to mean a polynucleotide that encodes a polypeptide related to a full length native M protein but does not encode one of the full length native M proteins.

In one aspect, the present invention is an M protein-like polypeptide containing an amino acid sequence that is at least 26% similar to amino acids 47–229 of SEQ ID NO:1. Preferably, the M protein-like polypeptide contains an amino acid sequence that is at least 45%, 50%, 60%, 70%, 80%, 90% or 95% similar to amino acids 47–229 of SEQ ID NO:1.

In another aspect, the present invention is an M protein gene-like polynucleotide containing a nucleotide sequence that encodes a polypeptide at least 26% similar to amino acids 47–229 of SEQ ID NO:1. Preferably, the M protein gene-like polynucleotide contains a nucleotide sequence that encodes a polypeptide at least 45%, 50%, 60%, 70%, 80%, 90% or 95% similar to amino acids 47–229 of SEQ ID NO:1. The M protein gene-like polynucleotide can be operably linked to a non-native promoter for controlling the expression of the polynucleotide. The promoter may be an inducible promoter or a tissue-specific promoter. The present invention also encompasses a vector and a host cell that contain the M protein gene-like polynucleotide.

In another aspect, the present invention is a method for inhibiting transport of RNA, proteins, and RNA-protein complexes between the nucleus and cytoplasm of a cell by exposing the cell to a sufficient amount of a VSV M protein-like polypeptide of the present invention. Preferably, the VSV M protein-like polypeptide used is selected from amino acids 47–229 of the VSV M protein and a vesiculovirus M protein. The vesiculovirus M protein is preferably the M protein of CV, SVCV and PV, and most preferably, the M protein of CV.

There are many ways known to one of ordinary skill in the art to expose a cell to a polypeptide and any of these ways can be used in the present invention. For example, for exposing a cell to a VSV M protein-like polypeptide in vitro (outside a living animal), an expression vector for the VSV M protein-like polypeptide can be constructed and introduced into the cell to express the polypeptide. Selection markers and inducible or tissue-specific promoters may be used in the vectors. A VSV M protein-like polypeptide can also be extracted from its native virions or a host cell that has been genetically engineered to synthesize the polypeptide. The extracted polypeptide can then be injected into the cell directly.

For exposing a cell to a VSV M protein-like polypeptide in vivo (in a living animal), one also typically has the option of administering a DNA construct for expressing the polypeptide or the polypeptide itself. As an example, the former can involve microinjecting a nucleic acid that contains a coding sequence for the polypeptide or administering a vector such as a virus-derived vector suitable for delivering and expressing a polynucleotide encoding the polypeptide; the latter can involve appropriately formulating the polypeptide for in vivo use and administer the formulated polypeptide into the body of an animal.

A VSV M protein-like polypeptide of the present invention needs to enter into the nucleus of a cell to function as an inhibitor of nucleocytoplasmic transport. As described in the examples below, certain amino acids of the polypeptide that are important for nuclear localization may not be important for transport inhibition activity. VSV M protein-like polypeptides of the present invention encompass polypeptides that have inhibition activity but lack nuclear localization capability. When used to inhibit nucleocytoplasmic transport, these polypeptides can either be injected into the nucleus of a cell directly or be connected to a nonnative nuclear localization sequence for entering into the nucleus. It is well within the capability of one of ordinary skill in the art to inject a polypeptide into the nucleus of a cell or to use a nuclear localization sequence to bring a polypeptide into the nucleus.

We envision that a variety of cell types will be useful for the present invention. Particularly, cancer cells, which are rapidly dividing, are a preferred cell type and may be particularly sensitive to small amounts of VSV M protein-like polypeptides because these cells must carry out nucleocytoplasmic transport at high levels. Therefore, one advantageous use of the present invention would be to treat a cancer-stricken organism or animal with a VSV M protein-like polypeptide in a manner that does not adversely affect normally growing cells but does inhibit nucleocytoplasmic transport of RNA and proteins in the rapidly growing cancer cells.

Other eukaryotic cells are suitable for the present invention. For example, one can inhibit nucleocytoplasmic transport of parasitic eukaryotes such as yeasts, protozoa or invertebrate metazoans. Therefore, another advantageous use of the present invention would be to treat a pathogen-infected organism or animal with a VSV M protein-like polypeptide in a manner that does not adversely affect normally growing cells but does inhibit nucleocytoplasmic transport of RNA and proteins in the parasitic cells.

The present invention discloses many VSV M protein-like polypeptides that possess nucleocytoplasmic transport inhibition activity. The transport inhibition efficacy of these different polypeptides for different cell types may very well be different. Thus, the present invention provides a pool of candidate peptides that may inhibit nucleocytoplasmic transport of one cell type such as cancer cells more than that of another cell type such as normal cells. One of ordinary skill in the art can easily test these polypeptides for differential efficacy. Once one finds differential efficacy—for example, if a parasitic cell reacts more favorably to a particular VSV M protein-like polypeptide than a mammalian cell—would wish to use this advantageous polypeptide in a therapeutic manner. One could treat a parasite-infected patient with a therapeutic dose of the VSV M protein-like polypeptide. The dose would inhibit nucleocytoplasmic transport in the parasite but not harm the patient.

We envision that one may wish to examine an M protein-like polypeptide of the present invention to determine a smaller fragment that still possesses the ability to inhibit nucleocytoplasmic transport. One of ordinary skill in the art of molecular biology would know how to create the necessary mutations to determine which regions of the polypeptide are necessary for inhibition of nucleocytoplasmic transport and could determine which regions to delete without undue experimentation, thereby reducing the size of the polypeptide without abolishing its ability to inhibit transport. Smaller fragments of an M protein-like polypeptide so identified will add to the candidate polypeptide pool for differential inhibition of nucleocytoplasmic transport in various cell types.

Inhibition of protein, RNA or RNA-protein complex transport may be measured by methods known to one of ordinary skill in the art or by methods disclosed below in the examples. The examples below disclose preferred methods.

In a related aspect, the present invention is a method for screening for an agent that can alter the nucleocytoplasmic transport inhibition activity of an M protein. An agent that enhances the transport inhibition activity of an M protein may be used in conjunction with the protein to increase inhibition efficiency. An agent that attenuates the inhibition activity of an M protein may be used in an animal to relieve symptoms associated with an infection by viruses that produce the M protein.

M proteins can inhibit nuclear import of proteins and RNA/protein complexes (17, 38). Thus, the present invention can be used for identifying nuclear import elements that are resistant to such inhibition. To do this, one would expose a cell to a sufficient quantity of a VSV M protein-like polypeptide such that nuclear import of proteins or RNA/protein complexes is impeded. Then, one would generate or select protein molecules that are imported into the nucleus of the cell. Next, the selected proteins would be analyzed to identify the nuclear import sequences that are attached to the imported proteins. For example, deletion mutants can be made from a selected protein to identity the sequences the deletion of which causes the remainder of the protein less importable in the presence of the VSV M protein-like polypeptide. These sequences are candidates for nuclear import elements and are further examined for their nuclear import function by attaching them to other proteins that are otherwise not imported to determine whether they can bring these proteins into the nucleus of a cell.

In another aspect, the M protein-like polypeptides of the present invention can be used to identify nuclear export elements as described in U.S. Pat. No. 5,888,727, which is hereby incorporated by reference in its entirety.

In yet another aspect, the present invention is the fragment of VSV M protein from amino acid 1 to amino acid 57 or from amino acid 23 to amino acid 57. A polynucleotide that encodes one of the above fragments is also within the scope of the present invention. As shown in the examples below, we have demonstrated that in addition to the full length VSV M protein (amino acids 1–229) and the fragment of VSV M protein from amino acid 47 to amino acid 229, fragments of amino acids 1–57 and 23–57 could also enter into the nucleus of a cell. We have shown that the full length VSV M protein, as well as the three fragments of the VSV M protein listed above, could bring another polypeptide into the nucleus of a cell. One can bring another polypeptide into the nucleus of a cell by making a chimeric protein linking the polypeptide to either the VSV M protein or one of the three fragments. The chimeric protein and a polynucleotide containing a nucleotide sequence that encodes the chimeric protein are within the scope of the present invention.

EXAMPLE 1

Materials and Methods

Sequence and Secondary Structure Analysis. Sequence similarity searches were performed with the BLAST program against the nonredundant database with the BLOSUM62 scoring matrix (19). The multiple sequence alignment was constructed by using CLUSTAL W (20). Secondary structure predictions for the individual M proteins were carried out by using the Ph.D. program and a consensus generated for the multiple sequence alignment (21). The PREDATOR program was used to generate a secondary structure prediction based on the multiple alignment (22, 23).

DNA Plasmids, Mutagenesis, Recombinant Protein Expression, and Purification. The pSP64poly(A)-VSV-M, pGEX-VSV-M, and pEGFP-VSV-M (Orsay strain) DNAs have been described (17). The pBSK plasmid encoding the CV M gene was kindly provided by A. C. Marriott (University of Warwick, Warwick, U.K.). To generate pSP64poly(A)CV-M, an RsaI fragment of pBSK-CV-M containing the CV M coding region was ligated to SmaI cut pSP64poly(A). To generate pGEX-CV-M, the CV M coding region was PCR amplified by using primers that contained SmaI restriction sites. The resulting PCR product was cut and ligated into the similarly cut pGEX vector. pEGFP-CV-M DNA was generated by subcloning the coding region of the CV M protein-containing fragment from pGEX-CV-M into the pEGPF-C1 vector (CLONTECH, Pal Alto, Calif.). DNA encoding the SVCV M protein was obtained by PCR amplification of an SVCV cDNA library kindly provided by J. C. Leong (Oregon State University, Corvallis, Oreg.). To generate pSP64poly(A)-SVCV-M, the resulting PCR product was cleaved with XbaI and SmaI and ligated to SmaI cut pSP64poly(A) DNA. To generate pGEX-SVCV-M, the SVCV M coding region was PCR amplified by using primers that contained EcoRI and BamHI restriction sites. The resulting PCR product was cut and ligated into the similarly cut pGEX vector. pEGFP-SVCV-M DNA was generated by subcloning the coding region of the SVCV M protein-containing fragment from pGEX-SVCV-M into the pEGPF-C1 vector.

All point mutations were generated by two-step PCR as described (17). The mutations were introduced into the M genes in the pGEX-M vectors and then subsequently subcloned into the pEGPF-C1 vector. Mutations were confirmed by DNA sequencing.

Recombinant glutathione S-transferase (GST)-M proteins were prepared as described (17).

In Vitro Transcription. DNA templates for in vitro transcription of U1, U1Sm, U5, and U6 snRNAs, U3 small nucleolar RNA (snoRNA), adenovirus major late mRNA, U6 RRE, ET202 RNA, and tRNAMet were generated as described (17, 24, 25). The template for transcription of constitutive transport element (CTE) RNA (CTE250, MPMV nucleotides 8007–8240) is described (24, 26). In vitro synthesis of [α-$^{32}$P]GTP-labeled RNAs was performed in 20 μl reactions as detailed elsewhere (27). For in vitro synthesis of poly(A)+ mRNAs encoding the various M proteins, plasmid DNAs were linearized with EcoRI and used in large-scale transcription reactions with SP6 polymerase according to the protocol of Promega (Madison, Wis.).

Expression and Detection of M Proteins in *Xenopus laevis* Oocytes. For in vivo expression and labeling of M proteins, mRNAs encoding M proteins were injected into the cytoplasms of stage VI oocytes and incubated for 16–24 h in MBS-H containing 0.25 μCi/μl (in 100 μl for 10 oocytes; 1 Ci=37 GBq) of [$^{35}$S]methionine (Amersham Biosciences, Piscataway, N.J.) (28). The nuclear and cytoplasmic fractions from such oocytes were analyzed as described (17).

Analysis of RNA and Protein Transport in *X. laevis* Oocytes. Preparation and injection of *X laevis* oocytes were as described (28). Approximately 20 fmol of mRNAs encoding the various M proteins were injected into the cytoplasm 18 h before the injection of import or export substrates. In other experiments, purified GST-M proteins (10 nl at 100 μg/ml) were injected directly into the nucleus, as indicated.

RNA mixtures (15 nl) containing 5 fmol of $^{32}$P-labeled import or export substrates were injected into either the cytoplasm or nucleus of oocytes, respectively. GST-Rev protein (10 nl at 100 μg/ml) was injected into the nuclei of oocytes. GST-SV40 nuclear localization signal (NLS)-GFP and GST-nucleoplasmin (NP) NLS-GFP were kindly provided by S. Adam (Northwestern University) and were injected (10 nl at 100 μg/ml) into the cytoplasm of oocytes. Blue dextran and U3 snoRNA were included in all injection mixtures as controls for injection and dissection accuracy. At the indicated time points, the oocytes were dissected into cytoplasmic and nuclear fractions and analyzed by PAGE followed by autoradiography or Western blotting as described (17).

Antibodies and Western Blotting. Mouse monoclonal anti-GST and anti-GFP antibodies were from Amersham Biosciences and Santa Cruz Biotechnology (Santa Cruz, Calif.), respectively. For Western blot analysis, extracts of oocytes or HeLa cells were fractionated by SDS/PAGE, and the proteins were transferred to Immobilon-P poly (vinylidene difluoride) membranes (Millipore, Bedford, Mass.). Membranes were probed with antibodies in TBS-T (10 mM Tris.HCl, pH 8.0/150 mM NaCl/1 mM EDTA/ 0.25% Tween 20) containing 5% powdered milk.

DNA Transfections. For transient transfections of GFP-M DNAs into tissue culture cells, 4×105 HeLa cells in MEM containing 15% FCS were seeded onto coverslips 24 h before use. Transfections were carried out with 0.5–1 μg of pEGFP-M DNAs and 10 μl of Lipofectamine according to the protocol of Life Technologies (Grand Island, N.Y.); 24 h later, cells were processed for immunofluorescence.

Immunofluoresence. To process cells for immunofluorescence, cells were either fixed with 2% paraformaldehyde for 15 min before permeabilization with 0.5% Triton X-100 or extracted first with 0.5% Triton X-100 for 3 min followed by paraformaldehyde fixation (17). The activities of the GFP-M protein chimeras were determined after injection of the mRNAs encoding these proteins into oocyte cytoplasms.

Results

Sequence Comparison of the Vesiculoviral M Proteins. We showed previously that VSV M protein in the nucleus of *X. laevis* oocytes is a potent inhibitor of snRNA and spliced mRNA export and of snRNP import (17). To discover other proteins that might have similar activity, we searched published databases for proteins with overall sequence homology to the VSV M protein. Significant similarities were detected (FIG. 1) between the M proteins of VSV and other sequenced vesiculoviruses including CV, SVCV, and piry virus (PV). Similar amino acid homologies have been noted by others (29, 30). We detected no significant sequence similarities between the VSV M protein and cellular proteins.

Sequence comparison using the CLUSTAL W alignment program showed that the vesiculoviral M proteins, as a group, share 11% identity and 29% similarity (FIG. 1). With respect to the M protein of VSV, the M proteins of CV, SVCV, and PV are 51.5%, 49%, and 49.8% similar. Sequence relatedness is highest between the M proteins from CV and PV (70.3%) and lowest between the M proteins from CV and SVCV (48%). The resemblance of the M proteins to one another encouraged us to test whether M proteins from other vesiculoviruses could inhibit nucleocytoplasmic transport.

The Vesiculoviral M Proteins Block Nucleocytoplasmic Transport of snRNAs, Spliced mRNA, and snRNPs. To express the vesiculoviral M proteins in Xenopus oocytes, DNAs encoding the M proteins of VSV, SVCV, and CV (PV cDNA was not available) were used as templates for in vitro synthesis of mRNAs. Upon injection into the cytoplasms of Xenopus oocytes, these mRNAs directed synthesis of $^{35}$S-methionine-labeled proteins with molecular weights in the range expected. Like the VSV M protein, the SVCV and CV M proteins were present in both the cytoplasms and the nuclei of the oocytes. The overall incorporation of labeled methionine into CV M protein was lower than that of either VSV or SVCV M protein, although the three proteins have comparable numbers of methionines (FIG. 1); thus, CV M protein accumulates to a lower level, under these conditions.

The abilities of the vesiculoviral M proteins to inhibit nuclear export and import were assayed by using several types of transport cargoes. All three M proteins made in oocytes blocked nuclear export of both U1 snRNA and spliced adenovirus major late mRNA for at least 20 h. Similarly, they all blocked export of the RNAs upon injection into oocyte nuclei as recombinant GST fusion proteins. The M proteins also blocked the import of U1, U5, and U6 snRNPs, which use different import pathways. Thus, the ability to inhibit nucleocytoplasmic transport is conserved between the M proteins of the vesiculoviruses.

The Vesiculoviral M Proteins Do Not Inactivate Transport Receptors. The effect of the M proteins on additional transport cargoes was monitored to determine whether the M proteins block movement of snRNAs, spliced mRNAs, and snRNPs by disabling required transport receptors or factors. CRM1 is the receptor that is responsible for the export of both snRNAs and proteins containing leucine-rich export signals such as the HIV-1 Rev protein (31). The factor TAP has been implicated in the export of both spliced mRNA and RNAs containing the CTE of Mason-Pfizer monkey virus (24, 26, 32, 33). The import receptor importin β, in conjunction with cargo-specific adaptors, mediates import of both snRNPs and NLS-containing proteins (34, 35).

The M proteins slowed, but did not block, the transport of other cargoes that use these transport receptors and factors. For example, CRM1-dependent export of Rev protein continued at a reduced rate in the presence of the M proteins. Likewise, Rev-dependent export of U6 RNA containing the Rev-responsive element (U6 RRE) was only slowed by VSV M protein. TAP-mediated export of CTE RNA was slowed but not blocked by VSV and SVCV M proteins; at early times, export of CTE RNA was also prevented by CV M protein, but, because of the nuclear instability of CTE RNA, we could not determine whether export would have occurred at time points later than 8 h. Similarly, importin β-dependent import of proteins containing either canonical or bipartite NLSs was slowed but not blocked by each of the M proteins when injected into the nucleus as purified recombinant GST-fusion proteins. The continued function of transport pathways dependent on CRM1, TAP, and importin β shows that the block to transport snRNAs, spliced mRNAs, and snRNPs by the M proteins is unlikely to result from the inactivation of these nuclear transport receptors and factors.

A Hierarchy of Inhibitory Activities Exists Between the Vesiculoviral M Proteins. Quantitative differences between the abilities of the vesiculoviral M proteins to inhibit transport became apparent when we assayed the movement of cargoes whose transport was slowed but not blocked. These differences also were observed with the export of several other RNAs that use other transport receptors (25, 36, 37). ET-202 is an artificial RNA molecule selected for its ability to be exported in the presence of the VSV M protein; it has been shown to be transported by a pathway distinct from tRNA export (U.S. Pat. No. 5,888,727, and 25). The rate of export of ET-202 RNA was affected more by the CV M protein than the VSV and SVCV M proteins. Similarly, VSV and SVCV M proteins made in the oocytes had only a very small effect on the export of $tRNAi^{Met}$ and $tRNA^{Tyr}$ compared with that of CV M protein. The potency of CV M protein was not simply due to increased amounts of proteins because the CV M protein accumulated to the lowest protein levels when expressed in oocytes. Thus, a gradient of inhibitory activities exists with the M protein of CV>VSV>SVCV.

Conservation of an Essential Methionine in the Vesiculoviral M Proteins. As we demonstrated recently, the ability of VSV M protein to inhibit transport requires a methionine at position 51 (Met-51), and even a conservative change to leucine abolishes this inhibitory activity (17). Because a methionine is present in comparable locations of all of the vesiculoviral M proteins (FIG. 1), we tested whether these residues were functionally important by changing them to leucines in the context of the GST-M fusion proteins. Upon injection into oocyte nuclei, none of these mutant proteins blocked snRNA export, even though they were stable and distributed to both the nucleus and cytoplasm. Thus, the same essential function is probably served by Met-51 of VSV, Met-31 of SVCV, and Met-54 of CV.

Adjacent to the essential methionine in each of the M proteins is an acidic amino acid (FIG. 1), and VSV M protein maintained its inhibitory activity when the aspartic acid was changed to glutamic acid. We tested the importance of these residues in the context of GST-M fusion proteins by changing the charged amino acids to their respective amide amino acids or to alanine. Both VSV and SVCV M proteins were inactivated when this aspartic acid was neutralized. In contrast, the M protein of CV appeared to be active when the acidic amino acid Glu-55 was neutralized by mutation to glutamine or alanine. Because the CV M protein is such a potent inhibitor of transport, it is possible that a moderate decrease in activity might have escaped detection under our assay conditions.

Active M Proteins Can Associate with the Nuclear Rim. Previously, we showed that in transfected HeLa cells the wild-type VSV M protein associates with the nuclear rim but an inactive mutant protein does not, suggesting that a component of the NPC is a target for the M protein (17). Here, we monitored the intracellular localization of the different M proteins by transfecting HeLa cells with equivalent amounts of DNAs encoding the various wild-type and mutant GFP-M proteins. The cells were either fixed directly with paraformaldehyde or treated with Triton X-100 before fixation; the latter treatment allowed for visualization of proteins associated with the nuclear rim. As we observed for GFP-tagged VSV M protein, GFP-tagged CV M protein was detected in the nucleus, in the cytoplasm, and at the nuclear rim. In contrast, GFP-tagged SVCV M protein was not found at the nuclear rim; moreover, this fusion protein was inactive as an inhibitor of RNA export in oocyte assay, indicating that the GFP tag interferes with the function of the SVCV M protein.

Consistent with our previous report, the distributions of all GFP-tagged inactive mutant proteins derived from the VSV or CV M proteins differed from those of the active proteins in that they did not exhibit a readily detectable association with the nuclear rim. Upon extraction with Triton X-100, differences between active and inactive M proteins were more pronounced, with active M proteins displaying prominent nuclear rim association. In contrast, only small amounts of the inactive M proteins could be detected at the nuclear rim, even though the inactive M proteins were present in 10-fold higher amounts, as assayed by Western blotting. These results suggest that the inactive M proteins display a greatly reduced affinity for a component of the nuclear rim. Thus, prominent association with the nuclear rim correlates with the inhibitory activities of all three M proteins.

EXAMPLE 2

Materials and Methods

Construction of GFP3-M protein DNA plasmids. The pEGFP-C3 vector encoding three tandem copies of GFP (pEGFP3-C3) was kindly provided by Y. Lazebnik (Cold Spring Harbor Laboratory). The reading frame within the multiple cloning site of pEGFP3-C3 was shifted by inserting a duplex made from the following complimentary oligonucleotides: 5'-GGGCTGCAGAGATCTCCGC-3' (SEQ ID NO:6) and 5'-GGAGATCTCTGCAGCCCCGC-3' (SEQ ID NO:7). Oligos were gel purified, kinased using T4 DNA kinase (Promega, Madison, Wis.), annealed and ligated into pEGFP3-C3 that had been digested with SacII. Correct orientation of the insert was confirmed by DNA sequencing. The resulting plasmid, pEGFP3-C1, was used to make plasmids encoding all versions of GFP3-M proteins.

To make pEGFP3-M 1–229, a DNA fragment encoding M protein was released from pEGFP-C1-OM (17) by BamHI digestion. This fragment was ligated into pEGFP3-C1 that had also been digested with BamHI. All truncations of M protein for ligation into pEGFP3-C1 were made by PCR using pGEX-2T-OM (17) as template (see Table 1). PCR products were digested with BamH1 and ligated into pEGFP3-C1 that had also been digested with BamHI. Correct orientation and sequence of all clones was confirmed by DNA sequencing.

Construction of GST-HA-M protein DNA plasmids. To make a vector encoding GST with an HA epitope tag fused to the C-terminus, PCR was done using the vector pGEX-2T (Amersham Biosciences, Piscataway, N.J.) as template, and the following primers (5' and 3' respectively): 5'-GTCTATGGCCATCATACGTTA-3' (SEQ ID NO:8) and 5'-CGGGATCCAAGAGCGTAATCTGGAACATCGTAT GGGTAACGCGGAACCAGATCCG-3' (SEQ ID NO:9). The PCR product and the pGEX-2T vector were both digested with BalI and BamHI, and then ligated together to generate the vector pGEX-2T-HA. Presence and orientation of the insert was confirmed by DNA sequencing.

To make vector encoding GST-HA-M 1–229, a DNA fragment encoding M protein was released from pEGFP-C1-OM (17) by digestion with BamHI. This fragment was ligated into the vector pGEX-2T-HA that had also been digested with BamHI. Vector encoding GST-HA-M 47–229 was made using the same BamHI-digested PCR product (described above) used to make pEGFP3-M 47–229. This fragment was ligated into BamHI-digested pGEX-2T-HA vector. DNA sequencing was done to confirm the orientation and sequence of inserts.

Mutagenesis. Point mutations within M protein were made using the QuikChange Site-Directed Mutagenesis Kit (Stratagene, La Jolla, Calif.). To generate mutant GFP3 fusion proteins for transient transfection, the following templates were used: pEGFP3-M 1–229 and pEGFP3-M 47–229. To generate mutant GST fusion proteins for purification following overexpression in E. coli, pGEX-2T-HA-M 1–229 and pGEX-2T-HA-M 47–229 were used as templates. Oligonucleotides used are shown in Table 2. The presence of mutations was confirmed in all cases by DNA sequencing.

Transfections. One day prior to performing transient transfections in HeLa cells, a six-well tissue culture plate containing coverslips was seeded with 4×10⁵ cells per well. Transfections were done according to the Invitrogen protocol, using 1 µg of DNA and 8 µl of LipofectAMINE reagent (Invitrogen Life Technologies, Carlsbad, Calif.). Cells were processed for fluorescence 24 hours after transfection.

GST-HA-M protein purification. For production of recombinant proteins, all plasmids were transformed into E. coli BL21 cells. Cells were grown overnight at 37° C. in LB medium containing ampicillin. Overnight cultures were used to inoculate fresh LB-amp to an OD600 of 0.04. Cultures were grown at room temperature to an OD600 of about 0.6 and then induced for 8 hours with 1 mM IPTG. Cells were harvested and protein was affinity purified as previously described (17).

Analysis of RNA export in *Xenopus laevis* oocytes. Preparation and injection of stage VI *X. laevis* oocytes was as described (27, 28). Purified GST-M proteins (about 100 µg/ml), were injected into the nucleus (12 nl) or into the cytoplasm (24 nl) 1 hour prior to injection of RNA export substrates. RNA mix (12 nl) containing about 5 fmol of $^{32}$P-labeled RNAs was injected into each oocyte nucleus. As controls for the accuracy of injection and dissection, all injection mixes included blue dextran, and the RNA mix contained U3 snoRNA, an RNA that is not exported from the nucleus. Oocytes were manually dissected into cytoplasmic and nuclear fractions at indicated time points. RNA from each fraction was analyzed by PAGE and autoradiography as previously described (17).

Antibodies and Western blotting. Mouse monoclonal anti-GFP antibodies (Santa Cruz Biotechnology, Santa Cruz, Calif.) were used for Western blots. HeLa cell extracts were fractionated by SDS-PAGE, and proteins were transferred to Immobilon-P poly (vinylidene difluoride) membranes (Millipore, Bedford, Mass.). Membranes were probed with antibodies in TBS-T (10 mM Tris-HCl, pH 8.0, 150 mM NaCl, 1 mM EDTA, 0.25% Tween 20) containing 5% milk and developed using LumiGLO (KPL, Gailhersburg, Md.).

Fluorescence microscopy. Cells were processed for fluorescence microscopy by fixing with 3% paraformaldehyde for 20 min. To view protein associated with NPCs, cells were extracted first with 0.5% Triton X-100 for 3 min, and then fixed with paraformaldehyde for 20 min. Fluorescent proteins were visualized using the ×100 objective of an Axioplan 2 fluorescence microscope (Carl Zeiss, Inc., Thornwood, N.Y.).

TABLE 1

Oligonucleotides used to generate PCR products for ligation into pEGFP₃-C1 vector. For each oligonucleotide pair, the 5' oligo is listed first, with the 3' oligo below.

| Clone | Oligonucleotides | |
|---|---|---|
| PEGFP₃-M 1–57 | 5'-CATCATGGGATCCTTAAAGAAAGATTCTCGG-3' | (SEQ ID NO:10) |
| | 5'-CGGGATCCATGCGGATCATGAGTGTCC-3' | (SEQ ID NO:11) |
| PEGFP₃-M 1–22 | 5'-CATCATGGGATCCTTAAAGAAAGATTCTCGG-3' | (SEQ ID NO:12) |
| | 5'-AAGGATCCGATCCCTAATTTC-3' | (SEQ ID NO:13) |
| PEGFP₃-M 23–57 | 5'-CGGGATCCGCACCACCCCCTTATG-3' | (SEQ ID NO:14) |
| | 5'CGGGATCCATGCGGATCATGAGTGTCC-3' | (SEQ ID NO:15) |
| PEGFP₃-M 32–57 | 5'-TGGGATCCATGGAGTATGCTCCGAGCG-3' | (SEQ ID NO:16) |
| | 5'-CGGGATCCATGCGGATCATGAGTGTCC-3' | (SEQ ID NO:17) |
| PEGFP₃-M 23–47 | 5'-CGGGATCCGCACCACCCCCTTATG-3' | (SEQ ID NO:18) |
| | 5'-CGGGATCCTCCAAAATAGGATTTGTCAATT-3' | (SEQ ID NO:19) |
| PEGFP₃-M 47–229 | 5'-CGGGATCCGGAGTTGACGAGATGGAC-3' | (SEQ ID NO:20) |
| | 5'-GGGAGCTCGCCCGGGGATCC-3' | (SEQ ID NO:21) |
| PEGFP₃-M 57–229 | 5'-CGGGATCCCATCAATTAAGATATGAGAAAAA-3' | (SEQ ID NO:22) |
| | 5'-GGGAGCTCGCCCGGGGGGATCC-3' | (SEQ ID NO:23) |
| PEGFP₃-M 47–194 | 5'-CGGGATCCGGAGTTGACGAGATGGAC-3' | (SEQ ID NO:24) |
| | 5'-CGGGATCCATTGAAATCATCCCAGAT-3' | (SEQ ID NO:25) |

TABLE 2

Oligonucleotides used to generate point mutations
in M protein amino acid sequence.
For each pair of oligonucleotides,
the 5' oligo is listed first, with the 3' oligo below.

| Amino Acid Substitution | Oligonucleotides | |
|---|---|---|
| P24A | 5'-CTAAGAAATTAGGGATCGCAGCACCCCCTTATGAAGAGGAC-3' | (SEQ ID NO:26) |
|  | 5'-GTCCTCTTCATAAGGGGGTGCTGCGATCCCTAATTTCTTAG-3' | (SEQ ID NO:27) |
| P25A | 5'-GAAATTAGGGATCGCACCAGCCCCTTATGAAGAGGACAC-3' | (SEQ ID NO:28) |
|  | 5'-GTGTCCTCTTCATAAGGGGCTGGTGCGATCCCTAATTTC-3' | (SEQ ID NO:29) |
| Y27A | 5'-GGGATCGCACCACCCCCTGCTGAAGAGGACACTAAC-3' | (SEQ ID NO:30) |
|  | 5'-GTTAGTGTCCTCTTCAGCAGGGGGTGGTGCGATCCC-3' | (SEQ ID NO:31) |
| A39L | 5'-GGAGTATGCTCCGAGCCTTCCAATGACAAATCCTATTTTGG-3' | (SEQ ID NO:32) |
|  | 5'-CCAAAATAGGATTTGTCATTGGAAGGCTCGGAGCATACTCC-3' | (SEQ ID NO:33) |
| P40A | 5'-GGAGTATGCTCCGAGCGCTGCAATTGACAAATCCTATTTTGG-3' | (SEQ ID NO:34) |
|  | 5'-CCAAAATAGGATTTGTCAATTGCAGCGCTCGGAGCATACTCC-3' | (SEQ ID NO:35) |
| M51A | 5'-CCTATTTTGGAGTTGACGAGGCGGACACTCATGATCCGC-3' | (SEQ ID NO:36) |
|  | 5'-CCTATTTTGGAGTTGACGAGGCGGACACTCATGATCCGC-3' | (SEQ ID NO:37) |
| P77A | 5'-GACGGTTAGATCTAATCGTGCGTTCAGAACATACTCAGAAG-3' | (SEQ ID NO:38) |
|  | 5'-CTTCTGAGTATGTTCTGAACGCACGATTAGATCTAACCGTC-3' | (SEQ ID NO:39) |
| W91A | 5'-GGCAGCCGCTGTATCCCATGCGGATCACATGTACATCGG-3' | (SEQ ID NO:40) |
|  | 5'-CCGATGTACATGTGATCCGCATGGGATACAGCGGCTGCC-3' | (SEQ ID NO:41) |
| Y95A | 5'-GTATCCCATTGGGATCACATGGCCATCGGAATGGCAGGGAAACG-3' | (SEQ ID NO:42) |
|  | 5'-CGTTTCCCTGCCATTCCGATGGCCATGTGATCCCAATGGGATAC-3' | (SEQ ID NO:43) |
| G97A | 5'-GGGATCACATGTACATCGCAATGGCAGGGAAACGTCCC-3' | (SEQ ID NO:44) |
|  | 5'-GGGACGTTTCCCTGCCATTGCGATGTACATGTGATCCC-3' | (SEQ ID NO:45) |
| K101A | 5'-CATCGGAATGGCAGGGGCACGTCCCTTCTACAAGATC-3' | (SEQ ID NO:46) |
|  | 5'-GATCTTGTAGAAGGGACGTGCCCCTGCCATTCCGATG-3' | (SEQ ID NO:47) |
| F104A | 5'-GGCAGGGAAACGTCCCGCCTACAAGATCTTGGCTTTTTTGGG-3' | (SEQ ID NO:48) |
|  | 5'-CCCAAAAAAGCCAAGATCTTGTAGGCGGGACGTTTCCCTGCC-3' | (SEQ ID NO:49) |
| Y105A | 5'-GCAGGGAAACGTCCCTTCGCCAAGATCTTGGCTTTTTTGGG-3' | (SEQ ID NO:50) |
|  | 5'-CCCAAAAAAGCCAAGATCTTGGCGAAGGGACGTTTCCCTGC-3' | (SEQ ID NO:51) |
| Y105F | 5'-GCAGGGAAACGTCCCTTCTTCAAGATCTTGGCTTTTTTGGG-3' | (SEQ ID NO:52) |
|  | 5'-CCCAAAAAAGCCAAGATCTTGAAGAAGGGACGTTTCCCTGC-3' | (SEQ ID NO:53) |
| K117A | 5'-GGGTTCTTCTAATCTAGCGGCCACTCCAGCGGTATTGGC-3' | (SEQ ID NO:54) |
|  | 5'-GCCAATACCGCTGGAGTGGCCGCTAGATTAGAAGAACCC-3' | (SEQ ID NO:55) |
| Y131A | 5'-GATCAAGGTCAACCAGAGGCTCACGCTCACTGTGAAGGC-3' | (SEQ ID NO:56) |
|  | 5'-GCCTTCACAGTGAGCGTGAGCCTCTGGTTGACCTTGATC-3' | (SEQ ID NO:57) |
| G137A | 5'-GTATCACGCTCACTGTGAAGCCAGGGCTTATTTGCCACAC-3' | (SEQ ID NO:58) |
|  | 5'-GTGTGGCAAATAAGCCCTGGCTTCACAGTGAGCGTGATAC-3' | (SEQ ID NO:59) |
| H143A | 5'-GGCAGGGCTTATTTGCCAGCCAGAATGGGGAAGACCCCTCCC-3' | (SEQ ID NO:60) |
|  | 5'-GGGAGGGGTCTTCCCCATTCTGGCTGGCAAATAAGCCCTGCC-3' | (SEQ ID NO:61) |
| G146A | 5'-GCTTATTTGCCACACAGAATGGCGAAGACCCCTCCCATGC-3' | (SEQ ID NO:62) |
|  | 5'-GCATGGGAGGGGTCTTCGCCATTCTGTGTGGCAAATAAGC-3' | (SEQ ID NO:63) |
| P149A | 5'-CACAGAATGGGGAAGACCGCTCCCATGCTCAATGTACC-3' | (SEQ ID NO:64) |
|  | 5'-GGTACATTGAGCATGGGAGCGGTCTTCCCCATTCTGTG-3' | (SEQ ID NO:65) |
| E156A | 5'-CCCATGCTCAATGTACCAGCGCACTTCAGAAGACCATTC-3' | (SEQ ID NO:66) |
|  | 5'-GAATGGTCTTCTGAAGTGCGCTGGTACATTGAGCATGGG-3' | (SEQ ID NO:67) |
| F158A | 5'-GCTCAATGTACCAGAGCACGCCAGAAGACCATTCAATG-3' | (SEQ ID NO:68) |
|  | 5'-CATTGAATGGTCTTCTGGCGTGCTCTGGTACATTGAGC-3' | (SEQ ID NO:69) |
| G169A | 5'-CAATGTAGGTCTTTACAAGGCAACGGTTGAGCTCAC-3' | (SEQ ID NO:70) |
|  | 5'-GTGAGCTCAACCGTTGCCTTGTAAAGACCTACATTG-3' | (SEQ ID NO:71) |
| G209A | 5'-GAGAAGGCCTTAATGTTTGCCCTGATTGTCGAGAAAAAGGC-3' | (SEQ ID NO:72) |
|  | 5'-GCCTTTTTCTCGACAATCAGGGCAAACATTAAGGCCTTCTC-3' | (SEQ ID NO:73) |
| L210A | 5'-GAAGGCCTTAATGTTTGGCGCGATTGTCGAGAAAAGGC-3' | (SEQ ID NO:74) |
|  | 5'-GCCTTTTTCTGACAATCGCGCCAAACATTAAGGCCTTC-3' | (SEQ ID NO:75) |

Results

M protein has an NLS within amino acids 47–229. Since nuclear localization is essential for M protein inhibitory activity, it is important to understand how this viral protein enters the nucleus. To determine whether M protein enters the nucleus by an active process or by passive diffusion, M protein localization was monitored upon fusion to a large cytoplasmic reporter protein, three tandem copies of Green Fluorescent Protein (GFP3). The cytoplasmic localization of GFP3 is presumed to be due to its size (about 72 Kd), which exceeds the diffusion limit of the NPC (1, 2). Fusion proteins were expressed in HeLa cells by transient transfection, and protein localization was visualized in fixed cells by fluorescence microscopy. The stability of GFP3-M fusion proteins was confirmed by Western blot analysis.

While GFP3 had a steady-state localization almost exclusively within the cytoplasm, fusion of M protein to this reporter resulted in a protein (GFP3-M 1–229) that accumulated within the nucleus. The ability of M protein to direct localization of a cytoplasmic protein into the nucleus demonstrates that M protein contains an NLS, and suggests that M protein can be actively imported into the nucleus.

To identify amino acid sequences within M protein that are necessary for nuclear localization, we examined the localization of truncated versions of M protein expressed in HeLa cells as GFP3 fusion proteins. A truncated version of M protein (GFP3-M 47–229) was made based on previous reports that M protein lacking amino acids 1–43 exists in a stable, trypsin-resistant conformation (39). We found that GFP3-M 47–229 accumulated within HeLa cell nuclei, demonstrating that M protein amino acids 47–229 are sufficient for nuclear localization.

To define a minimal NLS within M 47–229, further truncations were designed using a computer prediction of M protein structure (40) to increase the likelihood of generating stable proteins with minimal disruption of secondary structure. Sequence was deleted from either the amino- or carboxy-terminal ends of M 47–229 to generate GFP3-M 57–229 and GFP3-M 47–194, respectively. Neither of these proteins accumulated within the nuclei of HeLa cells following transient transfection. Thus, sequence elements within both M 47–57 and M 194–229 are necessary, but neither element alone is sufficient, for function of the NLS within M 47–229.

Trp-91 and Tyr-105 are important for the nuclear localization of M 47–229. An alignment of the amino acid sequences of M proteins from several Vesiculovirus family members are presented in FIG. 1. Amino acids conserved among the M proteins are highlighted in bold-type. Conserved amino acids are likely to be important for protein function, structure and/or stability. In the example 1 above, we showed that a conserved Met at position 51 is essential for the inhibitory activity of all three M proteins tested, as well as for the association of these M proteins with NPCs. Therefore, we reasoned that one or more of the conserved amino acids might also be important for nuclear localization, since this process is necessary for the inhibitory activity of M protein. To confirm this, single alanine substitutions were made at each conserved residue within the region of M protein that was sufficient for nuclear localization, M 47–229. Mutant proteins were expressed in HeLa cells as GFP3 fusion proteins, and fluorescence microscopy was used to visualize protein localization. Lysates from cells expressing fusion proteins were analyzed by Western blot to confirm protein stability.

Of the nineteen conserved amino acids mutated to alanine in the context of GFP3-M 47–229, two amino acids were identified as having a significant effect on nuclear localization. All other conserved amino acids, when mutated to alanine, had little or no effect on nuclear localization. Alanine substitutions at either position 91 (W91A) or position 105 (Y105A) within GFP3-M 47–229 resulted in protein that localized mainly to the cytoplasm. By contrast, a conservative substitution made at position 105 (Y105F) had no apparent effect on nuclear localization of the protein, compared to that of wild type protein. This data demonstrates that amino acids at positions 91 and 105 are important for the nuclear localization of M 47–229. In addition, at position 105, the presence, and not the identity, of an aromatic residue is important.

Regions of M protein necessary for activity are distinguishable from regions necessary for nuclear localization. To test whether M 47–229 is sufficient for inhibitory activity, a recombinant fusion protein was made for injection into Xenopus oocytes. GST containing an HA epitope tag at its C-terminus (GST-HA) was fused to M 47–229 to generate GST-HA-M 47–229. We have previously shown that a fusion protein containing GST and the full-length M protein (GST-M 1–229) inhibits export of snRNA and mRNA when injected into oocyte nuclei or cytoplasms (17). Likewise, GST-HA-M 1–229 had inhibitory activity. Similarly, GST-HA-M 47–229 was active as an inhibitor of snRNA and mRNA export when injected into the nucleus, or when injected into the cytoplasm. Therefore, M 47–229 is sufficient, not only for nuclear localization, but also for inhibitory activity.

We asked whether the amino acids we had identified as being important for nuclear localization of M 47–229, Trp-91 and Tyr-105, were also important for M protein inhibitory activity. To address this question, GST-HA-M 47–229 containing either W91A or Y105A was assayed for inhibitory activity. We have found that, upon injection into oocyte nuclei, both mutant proteins inhibited snRNA and mRNA export, indicating that Trp-91 and Tyr-105 are not necessary for M protein activity. Notably, in the presence of either mutant protein, there was a low level of snRNA and mRNA present in the cytoplasm at the second time point. While this indicates that the mutant proteins may not be as potent as WT protein, they do retain inhibitory activity, since, compared to control, there was less mRNA and snRNA in cytoplasms of oocytes treated with mutant M proteins. Therefore, because Trp-91 and Tyr-105 are important for nuclear localization, but less so for inhibitory activity, regions of M protein necessary for activity are distinct from regions of M protein necessary for nuclear localization.

We asked whether GFP3-M 47–229 associated with NPCs. NPC-associated protein was visualized by treating transfected cells with Triton X-100 before fixing to release soluble nuclear and cytoplasmic protein, while leaving nuclear pore-associated protein intact (17). While wild type GFP3-M 47–229 associated with NPCs, GFP3-M 47–229 containing alanine substitutions at either position 91 or position 105 did not. These results are consistent with the conclusion that M 47–229 is sufficient for inhibitory activity, and with the observation that W91A and Y105A substitutions disrupt the ability of GFP3-M 47–229 to enter the nucleus, where association with component(s) of the NPC is thought to occur (16, 17, 38).

M protein has a second, novel NLS within amino acids 23–57. We asked what effect the W91A and Y105A substitutions had on nuclear localization of the full-length protein. To do this, alanine substitutions at positions 91 and 105 were made within GFP3-M 1–229 for expression in HeLa cells. We have found that an alanine substitution at position 105 (Y105A) greatly reduced nuclear localization of GFP3-M 1–229, demonstrating that Tyr-105 is important for nuclear localization of both M 47–229 and M 1–229. However, when a conservative substitution (Y105F) was made at position 105, in the context of GFP3-M 1–229, protein localized to the nucleus, similar to what was seen when this substitution was made in the context of GFP3-M 47–229. Thus, an aromatic residue is important at position 105 for nuclear localization of both M 1–229 and M 47–229.

In contrast to what was seen with Y105A, W91A had no apparent effect on nuclear localization of GFP3-M 1–229. Therefore, while Trp-91 is important for the nuclear localization of M 47–229, it is not required for the nuclear localization of M 1–229. This result suggested that M protein might have a second NLS, perhaps within amino acids 1–46. Therefore, we tested whether sequences within M 1–46 could function as an NLS by expressing truncations of M 1–46 as GFP3 fusion proteins in HeLa cells (FIG. 2B).

FIG. 2A shows the first 57 amino acids of M protein. Residues identified previously as being conserved among M proteins of other Vesiculoviruses (FIG. 1) are highlighted in bold with position numbers above each. Clearly, this region of M protein contains several basic amino acids, a characteristic of the previously defined NLSs of SV40 large T Antigen and Nucleoplasmin (41–43). Surprisingly, while the basic residues of M 1–57 are mainly found within amino acids 1–22, GFP3-M 1–22 accumulated within the cytoplasm, demonstrating that this region is not sufficient for nuclear localization.

GFP3-M 1–47 was present within the nucleus, but did not strongly accumulate there. However, GFP3-M 1–57 did strongly accumulate within the nucleus, suggesting that this region of M protein contains an NLS. Similarly, GFP3-M 23–57 strongly accumulated within the nucleus. However, eliminating sequence from either end of this construct created GFP3-M 32–57 and GFP3-M 23–47, neither of which strongly accumulated within the nucleus. Therefore, the minimal amino-terminal NLS of M protein resides within amino acids 23–57. This sequence (underlined in FIG. 2A) is a novel NLS, as it has no homology to previously reported NLSs.

REFERENCES

1. Görlich, D. & Kutay, U. (1999) Annu. Rev. Cell Dev. Biol. 15, 607–660.
2. Mattaj, I. W. & Englmeier, L. (1998) Annu. Rev. Biochem. 67, 265–306.
3. Weis, K. (1998) Trends Biochem. Sci. 23, 185–189.
4. Wente, S. R. (2000) Science 288, 1374–1377.
5. Moore, M. S. (1998) J. Biol. Chem. 273, 22857–22860.
6. Dahlberg, J. E. & Lund, E. (1998) Curr. Opin. Cell Biol. 10, 400–408.
7. Izaurralde, E., Kutay, U., von Kobbe, C., Mattaj, I. W. & Görlich, D. (1997) EMBO J. 16, 6535–6547.
8. Dahlberg, J. E. & Lund, E. (1997) Semin. Cell Dev. Biol. 8, 65–70.
9. Powers, M. A., Forbes, D. J., Dahlberg, J. E. & Lund, E. (1997) J. Cell Biol. 136, 241–250.
10. Ullman, K. S., Shah, S., Powers, M. A. & Forbes, D. J. (1999) Mol. Biol. Cell 10, 649–664.
11. Kutay, U., Izaurralde, E., Bischoff, F. R., Mattaj, I. W. & Görlich, D. (1997) EMBO J. 16, 1153–1163.
12. Bachi, A., Braun, I. C., Rodrigues, J. P., Pante, N., Ribbeck, N., von Kobbe, C., Kutay, U., Wilm, M., Görlich, D., Carmo-Fonseca, M. & Izaurralde, E. (2000) RNA 6, 136–158.
13. Chen, Z., Li, Y. & Krug, R. M. (1999) EMBO J. 18, 2273–2283.
14. Dobbelstein, M., Roth, J. W., Kimberly, T., Levine, A. J. & Shenk, T. (1997) EMBO J. 16, 4276–4284.
15. Her, L-S., Lund, E. & Dahlberg, J. E. (1997) Science 276, 1845–1848.
16. von Kobbe, C., van Deursen, J. M., Rodrigues, J. P., Sitterlin, D., Bachi, A., Wu, X., Wilm, M., Carmo-Fonseca, M. & Izaurralde, E. (2000) Mol. Cell 6, 1243–1252.
17. Petersen, J. M., Her, L-S., Varvel, V., Lund, E. & Dahlberg, J. E. (2000) Mol. Cell. Biol. 20, 8590–8601.
19. Altschul, S. F., Gish, W., Miller, W., Myers, E. W. & Lipman, D. J. (1990) J. Mol. Biol. 215, 403–410.
20. Thompson, J. D., Higgins, D. G. & Gibson, T. J. (1994) Nucleic Acids Res. 22, 4673–4680.
21. Rost, B., Sander, C. & Schneider, R. (1994) Comput. Appl. Biosci. 10, 53–60.
22. Frishman, D. & Argos, P. (1996) Protein Eng. 9, 133–142.
23. Frishman, D. & Argos, P. (1997) Proteins 27, 329–335.
24. Pasquinelli, A. E., Ernst, R. K., Lund, E., Grimm, C., Zapp, M. L., Rekosh, D., Hammarskjöld, M. L. & Dahlberg, J. E. (1997) EMBO J. 16, 7500–7510.
25. Grimm, C., Lund, E. & Dahlberg, J. E. (1997) Proc. Natl. Acad. Sci. USA 94, 10122–10127.
26. Ernst, R. K., Bray, M., Rekosh, D. & Hammarskjöld, M. L. (1997) RNA 3, 210–222.
27. Pasquinelli, A. E., Dahlberg, J. E. & Lund, E. (1995) RNA 1, 957–967.
28. Gurdon, J. B. & Wickens, W. P. (1983) Methods Enzymol. 101, 370–386.
29. Barge, A., Gagnon, J., Chaffotte, A., Timmins, P., Langowski, J., Ruigrok, R. W. & Gaudin, Y. (1996) Virology 219, 465–470.
30. Taylor, A., Easton, A. J. & Marriott, A. C. (1999) Virus Genes 19, 223–228.
31. Fornerod, M., Ohno, M., Yoshida, M. & Mattaj, I. W. (1997) Cell 90, 1051–1060.
32. Gruter, P., Tabernero, C., von Kobbe, C., Schmitt, C., Saavedra, C., Bachi, A., Wilm, M., Felber, B. K. & Izaurralde, E. (1998) Mol. Cell 1, 649–659.
33. Kang, Y. & Cullen, B. R. (1999) Genes Dev. 13, 1126–1139.
34. Palacios, I., Hetzer, M., Adam, S. A. & Mattaj, I. W. (1997) EMBO J. 16, 6783–6792.
35. Chi, N. C., Adam, E. J. & Adam, S. A. (1995) J. Cell Biol. 130, 265–274.
36. Arts, G. J., Fornerod, M. & Mattaj, I. W. (1998) Curr. Biol. 8, 305–314.
37. Kutay, U., Lipowsky, G., Izaurralde, E., Bischoff F. R., Schwarzmaier, P., Hartmann, E. & Gorlich, D. (1998) Mol. Cell 1, 359–369.
38. Enninga, J., Levy, D. E., Blobel, G., and Fontoura, B. M. A. (2002) Science 295, 1523–1525.
39. Ogden, J. R., Pal, R. and Wagner, R. (1986) Journal of Virology, 860–868.
40. Petersen, J. M., Her, L-S., and Dahlberg, J. E. (2001) PNAS 98, 8590–8595.
41. Kalderon, D., Richardson, W. D., Markham, A. F., Smith, A. E. (1984) Nature 311, 33–38.
42. Lanford, R. E., Butel, J. S. (1984) Cell 37:801–813.
43. Robbins, J., Dilworth, S. M., Laskey, R. A., Dingwall, C. (1991) Cell 64:615–623.

We claim:

1. An isolated M protein-like polypeptide comprising an amino acid sequence that is at least 26% similar to amino acids 47–229 of SEQ ID NO:1, wherein the amino acid sequence contains methionine at a position corresponding to position 51 of SEQ ID NO:1.

2. The isolated M protein-like polypeptide of claim 1, wherein the amino acid sequence is at least 45% similar to amino acids 47–229 of SEQ ID NO:1.

3. The isolated M protein-like polypeptide of claim 1, wherein the amino acid sequence is at least 50% similar to amino acids 47–229 of SEQ ID NO:1.

4. The isolated M protein-like polypeptide of claim 1, wherein the amino acid sequence is at least 60% similar to amino acids 47–229 of SEQ ID NO:1.

5. The isolated M protein-like polypeptide of claim 1, wherein the amino acid sequence is at least 80% similar to amino acids 47–229 of SEQ ID NO:1.

6. An isolated M protein gene-like polynucleotide comprising:
    a nucleotide sequence that encodes a polypeptide at least 26% similar to amino acids 47–229 of SEQ ID NO:1, wherein the amino acid sequence contains methionine at a position corresponding to position 51 of SEQ ID NO:1.

7. The isolated M protein gene-like polynucleotide of claim 6, wherein the nucleotide sequence encodes a polypeptide that is at least 45% similar to amino acids 47–229 of SEQ ID NO:1.

8. The isolated M protein gene-like polynucleotide of claim 6, wherein the nucleotide sequence encodes a polypeptide that is at least 50% similar to amino acids 47–229 of SEQ ID NO:1.

9. The isolated M protein gene-like polynucleotide of claim 6, wherein the nucleotide sequence encodes a polypeptide that is at least 60% similar to amino acids 47–229 of SEQ ID NO:1.

10. The isolated M protein gene-like polynucleotide of claim 6, wherein the nucleotide sequence encodes a polypeptide that is at least 80% similar to amino acids 47–229 of SEQ ID NO:1.

11. An isolated nucleic acid comprising:
    the M protein gene-like polynucleotide of claim 6; and
    a non-native promoter linked to said polynucleotide in a way to control the expression of said polynucleotide.

12. A vector comprising the M protein gene-like polynucleotide of claim 6.

13. A cell comprising the M protein gene-like polynucleotide of claim 6.

14. A method for inhibiting transport of RNA, proteins or RNA-protein complexes between nucleus and cytoplasm of a cell comprising the step of exposing the cell to sufficient quantity of a VSV M protein-like polypeptide, wherein the polypeptide comprises an amino acid sequence that is at least 26% similar to amino acids 47–229 of SEQ ID NO:1 and the amino acid sequence contains methionine at a position corresponding to position 51 of SEQ ID NO:1, such that the transport of RNA, proteins or RNA-protein complexes between nucleus and cytoplasm of the cell is inhibited.

15. The method of claim 14, wherein the amino acid sequence is at least 45% similar to amino acids 47–229 of SEQ ID NO:1.

16. The method of claim 14, wherein the amino acid sequence is at least 50% similar to amino acids 47–229 of SEQ ID NO:1.

17. The method of claim 14, wherein the amino acid sequence is at least 60% similar to amino acids 47–229 of SEQ ID NO:1.

18. The method of claim 14, wherein the amino acid sequence is at least 80% similar to amino acids 47–229 of SEQ ID NO:1.

19. The method of claim 14, wherein the amino acid sequence further contains tryptophan and an aromatic residue at positions corresponding to positions 91 and 105 of SEQ ID NO:1.

20. The method of claim 19, wherein the aromatic residue is selected from tyrosine and phenylalanine.

21. The method of claim 20, wherein the VSV M protein-like polypeptide is a vesiculovirus M protein.

22. The method of claim 21, wherein the vesiculovirus is selected from chandipura virus (CV), spring viremia of carp virus (SVCV), and piry virus (PV).

23. The method of claim 22, wherein the vesiculovirus is CV.

24. The method of claim 14, wherein exposing a cell to a sufficient quantity of a VSV M protein-like polypeptide is achieved by synthesizing the VSV M protein-like polypeptide inside the cell.

25. The method of claim 14, wherein the VSV M protein-like polypeptide is obtained by extraction from the polypeptide's native virus or a host cell expressing the polypeptide.

26. A method for inhibiting transport of RNA, proteins or RNA-protein complexes between nucleus and cytoplasm of a cancer cell comprising the step of exposing the cancer cell to sufficient quantity of a VSV M protein-like polypeptide, wherein the polypeptide comprises an amino acid sequence that is at least 26% similar to amino acids 47–229 of SEQ ID NO:1 and the amino acid sequence contains methionine at a position corresponding to position 51 of SEQ ID NO:1, such that the transport of RNA, proteins or RNA-protein complexes between nucleus and cytoplasm of the cancer cell is inhibited.

27. A method for inhibiting import of proteins or RNA-protein complexes from cytoplasm into nucleus of a cell comprising the step of exposing the cell to sufficient quantity of a VSV M protein-like polypeptide, wherein the polypeptide comprises an amino acid sequence that is at least 26% similar to amino acids 47–229 of SEQ ID NO:1 and the amino acid sequence contains methionine at a position corresponding to position 51 of SEQ ID NO:1, such that the import of proteins or RNA-protein complexes from cytoplasm into nucleus of the cell is inhibited.

28. A method for inhibiting export of nucleic acids from nucleus to cytoplasm of a cell comprising the step of exposing the cell to sufficient quantity of a VSV M protein-like polypeptide, wherein the polypeptide comprises an amino acid sequence that is at least 26% similar to amino acids 47–229 of SEQ ID NO:1 and the amino acid sequence contains methionine at a position corresponding to position 51 of SEQ ID NO:1, such that the export of nucleic acids from nucleus to cytoplasm of the cell is inhibited.

29. A method for inhibiting transport of RNA, proteins or RNA-protein complexes between nucleus and cytoplasm of a cell comprising the step of:

analyzing an amino acid sequence that is at least 26% similar to amino acids 47–229 of SEQ ID NO:1 to determine a smaller fragment that retains the ability to inhibit nucleocytoplasmic transport, wherein fragments of the amino acid sequence are compared to determine which segments of the amino acid sequence can be deleted without loss of transport inhibition function; and exposing a cell to sufficient quantity of a VSV M protein-like polypeptide which comprises the smaller fragment such that transport of RNA, proteins or RNA-protein complexes across the nuclear envelope is inhibited.

30. A method for screening for an agent that can alter the activity of an M protein comprising the steps of:

introducing into the nucleus of a cell a VSV M protein-like polypeptide comprising an amino acid sequence that is at least 26% similar to amino acids 47–229 of SEQ ID NO:1, wherein the amino acid sequence contains methionine at a position corresponding to position 51 of SEQ ID NO:1, and wherein the polypeptide inhibits the transport of a molecule between the nucleus and cytoplasm of the cell and the molecule is selected from a RNA, a protein and a RNA-protein complex;

exposing the cell to a test agent; and determining the nucleocytoplasmic transport rate of the molecule before and after exposing the cell to the agent.

31. A method for identifying a nuclear export element comprising the steps of:

exposing a cell to sufficient quantity of an M protein-like polypeptide which comprises an amino acid sequence that is at least 26% similar to amino acids 47–229 of SEQ ID NO:1, wherein the amino acid sequence contains methionine at a position corresponding to position 51 of SEQ ID NO:1, so that export of RNA between the nucleus and cytoplasm is inhibited; and selecting an RNA molecule that is exported in the presence of the M protein-like polypeptide and examining the molecule for the presence of a nuclear export element.

32. A method for identifying a nuclear import element comprising the steps of:

exposing a cell to sufficient quantity of an M protein-like polypeptide which comprises an amino acid sequence that is at least 26% similar to amino acids 47–229 of SEQ ID NO:1, wherein the amino acid sequence contains methionine at a position corresponding to position 51 of SEQ ID NO:1, so that import of proteins from cytoplasm into the nucleus is inhibited; and selecting a protein molecule that is imported in the presence of the M protein-like polypeptide and examining the imported molecule for the presence of a polypeptide that can function as a nuclear export element when attached to another protein.

33. An isolated polypeptide consisting of an amino acid sequence selected from amino acids 1–57 of VSV M protein and amino acids 23–57 of VSV M protein.

34. An isolated polynucleotide consisting of a nucleotide sequence that encodes the polypeptide of claim 33.

35. A chimeric protein comprising a non-M protein polypeptide and a polypeptide having an amino acid sequence selected from amino acids 1–229 of VSV M protein, amino acids 47–229 of VSV M protein, amino acids 1–57 of VSV M protein, and amino acids 23–57 of VSV M protein.

36. An isolated nucleic acid comprising a nucleotide sequence that encodes the chimeric protein of claim 35.

37. A method for introducing a non-M protein polypeptide into the nucleus of a cell comprising the step of linking the non-M protein polypeptide to a second polypeptide having an amino acid sequence selected from amino acids 1–229 of VSV M protein, amino acids 47–229 of VSV M protein, amino acids 1–57 of VSV M protein, and amino acids 23–57 of VSV M protein such that the non-M protein polypeptide can enter into the nucleus of a cell along with the second polypeptide.

* * * * *